United States Patent [19]

Davis

[11] 4,347,148

[45] Aug. 31, 1982

[54] FULL AND LUBRICANT COMPOSITIONS CONTAINING NITRO PHENOLS

[75] Inventor: Kirk E. Davis, Euclid, Ohio

[73] Assignee: The Lubrizol Corporation, Wickliffe, Ohio

[21] Appl. No.: 95,290

[22] Filed: Nov. 19, 1979

Related U.S. Application Data

[63] Continuation-in-part of Ser. No. 705,653, Jul. 15, 1976, abandoned.

[51] Int. Cl.$^3$ .................. C10M 1/32; C10M 3/26; C10M 5/20; C10M 7/30

[52] U.S. Cl. .................. 252/51.5 R; 44/70; 44/71; 44/72; 44/78; 44/77; 44/79; 252/50; 252/51; 252/51.5 A; 564/156; 564/166; 568/630; 568/655; 568/706; 568/709; 568/711; 568/713

[58] Field of Search ............ 252/51.5 A, 51.5 R, 252/50, 51; 260/575; 562/434; 564/156, 166; 568/706, 709, 712, 630, 655, 711, 713; 44/70, 71, 77, 78, 79, 72

[56] References Cited

U.S. PATENT DOCUMENTS

| | | | |
|---|---|---|---|
| 2,054,276 | 9/1966 | Wilson, Jr. ........................... | 44/9 |
| 2,074,467 | 3/1937 | Gutzeit ................................ | 44/9 |
| 2,571,092 | 10/1951 | Wasserman ...................... | 260/575 X |
| 2,831,898 | 4/1958 | Ecke .................................. | 260/575 |
| 2,868,844 | 1/1959 | Coffield et al. ................. | 260/575 X |
| 3,368,972 | 2/1968 | Otto ............................ | 252/51.5 R X |
| 3,410,670 | 11/1968 | LeSuer ................................ | 44/69 |
| 3,413,347 | 11/1968 | Worrel ....................... | 252/51.5 R X |
| 3,434,814 | 3/1969 | Dubeck ............................ | 44/69 |
| 3,996,285 | 12/1976 | Culbertson ............... | 252/51.5 R X |

*Primary Examiner*—Helen M. S. Sneed
*Attorney, Agent, or Firm*—Ronald L. Lyons; William H. Pittman; John P. Ward

[57] ABSTRACT

Nitro phenols of the general formula

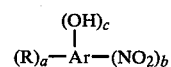

wherein R is an aliphatic substituent of at least about 40 carbon atoms, a, b and c are, for example, each 1, 2 or 3, and Ar is an aromatic moiety such as a benzene nucleus, naphthalene nucleus or linked benzene nuclei, are useful additives for fuels and lubricants and intermediates to such additives. These nitro phenols can be conveniently prepared by nitrating appropriate phenols. Typically nitro phenols are formed by nitration of alkyl phenols having an alkyl group of at least about 50 carbon atoms.

75 Claims, No Drawings

FULL AND LUBRICANT COMPOSITIONS CONTAINING NITRO PHENOLS

REFERENCE TO RELATED APPLICATIONS

This application is a continuation of earlier filed copending application Ser. No. 705,653, filed July 15, 1976 now abandoned.

The disclosure of this prior application is hereby incorporated by reference into this application in its entirety.

The amino phenols referred to in the subject application are not part of my invention, but rather are the invention of Richard Michael Lange, described in copending U.S. application Ser. No. 253,830, filed Apr. 13, 1981 and copending U.S. application Ser. No. 249,770, filed Apr. 1, 1981.

BACKGROUND OF THE INVENTION

1. Field of the Invention

This invention relates to additive compositions for use in lubricants based on oils of lubricating viscosity and normally liquid fuels and to intermediates for the preparation of such additives. More particularly, it relates to nitro phenols having at least one aliphatic substituent of at least about 40 aliphatic carbon atoms.

2. Prior Art

Certain nitro phenols are known in the prior art as exemplified by U.S. Pat. Nos. 2,197,835; 2,502,708; 2,571,092; 3,410,670; 3,410,798; 2,488,472; 2,618,538; and 3,897,352.

3. General Background

The improvement of the performance characteristics of lubricants based on oils of lubricating viscosity (e.g., oils and greases) and normally liquid fuels through the use of additives has been known for decades. Still, in these days of growing material shortages, spiralling equipment replacement costs, increasing fuel and lubricant costs, new types of engines, fuels and lubricants, and environmental consciousness, the search for new, effective, alternate lubricant and fuel additives continues unabated.

4. Objects

Therefore, it is an object of this invention to provide novel additive compositions that will impart useful and desirable properties to oil-based lubricants and normally liquid fuels.

It is a further object of this invention to provide novel concentrate, lubricant and fuel compositions containing novel nitro phenols.

Another object of this invention is to provide novel nitro phenols which can serve as intermediates and precursors for the production of lubricating oils and fuel additives and, ultimately, lubricant, fuel and concentrate compositions.

Other objects will be apparent to those skilled in the art upon review of the present specification.

SUMMARY OF THE INVENTION

This invention comprises nitro phenols of the formula

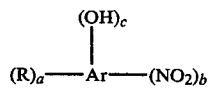

Formula I wherein R is an aliphatic substituent of at least 40 carbon atoms; at least one R is in a position ortho or para to at least one —OH substituent attached directly to Ar; a, b and c are each independently integers of 1 up to three times the number of aromatic nuclei in Ar with the sum a+b+c not exceeding the number of unsatisfied valences in Ar, and Ar is an aromatic moiety having 0 to 3 optional substituents selected from the group consisting of lower alkyl, lower alkoxyl, halo, carboxy, carboxy ester of mono- and dihydric $C_{1-7}$ alkanols, carboxamide wherein the amide nitrogen can have up to 1 or 2 $C_{1-7}$ alkyl substituents and combinations of any of said optional substituents.

The term "phenol" is used in this specification in its art-accepted, generic sense to refer to hydroxy-aromatic compounds having at least one hydroxyl group bonded directly to a carbon of an aromatic ring.

Lubricants based on oils of lubricating viscosity, normally liquid fuels and additive concentrates containing the above-described nitro phenols are included in the embodiments of this invention.

DESCRIPTION OF THE INVENTION

The aromatic moiety, Ar.

The aromatic moiety, Ar, can be a single aromatic nucleus such as a benzene nucleus, a pyridine nucleus, a thiophene nucleus, a 1,2,3,5-tetrahydronaphthalene nucleus, etc., or it can be a polynuclear aromatic moiety. Such polynuclear moieties can be of the fused type wherein an aromatic nucleus is fused at two points to another nucleus such as found in naphthalene, anthracene, azanaphthalene, etc. moieties. Polynuclear aromatic moieties also can be of the linked type wherein at least two nuclei (either mono or polynuclear) are linked through bridging linkages to each other. Such bridging linkages can be chosen from the group consisting of carbon-to-carbon single bonds, ether linkages, keto linkages, sulfide linkages, polysulfide linkages of 2 to 6 sulfur atoms, sulfinyl linkages, sulfonyl linkages, alkylene linkages, alkylidene linkages, lower alkylene ether linkages, alkylene keto linkages, lower alkylene sulfur linkages, lower alkylene polysulfide linkages of 2 to 6 carbon atoms, amino linkages, polyamino linkages and mixtures of such divalent bridging linkages. In certain instances, more than one bridging linkage can be present in Ar between two aromatic nuclei. For example, a fluorene nucleus has two benzene nuclei linked by both a methylene linkage and a covalent bond. Normally, Ar will contain only carbon atoms in the aromatic nuclei per se although in certain Ar moieties heterocyclic nuclei such as pyridyl, thienyl and furanyl nuclei can be present.

The number of aromatic nuclei, fused, linked or both, in Ar play a role in determining the integer values of a, b and c in Formula I. For example, when Ar contains a single aromatic nucleus, a, b and c are each independently 1 to 3. When Ar contains 2 aromatic nuclei, a, b and c can each be an integer of 1 to 6, that is, up to three times the number of aromatic nuclei present (in naphthalene, 2). With a trinuclear Ar moiety, a, b and c can each be an integer of 1 to 9. For example, when Ar is a triphenyl moiety, a, b and c can each independently be an integer of 1 to 9. The values of a, b and c are obviously limited by the fact that their sum cannot exceed the total unsatisfied valences of Ar.

The single ring aromatic nucleus which can be the Ar moiety can be represented by the general formula ar(Q)$_m$ wherein ar represents a single ring aromatic nucleus (e.g., benzene, pyridine or thiophene) of 4 to 6 carbons, each Q independently represents a lower alkyl group, lower alkoxy group or halogen atom, and m is 0 to 3. As used in this specification and appended claims, "lower" refers to groups having 7 or less carbon atoms such as lower alkyl and lower alkoxyl groups. Halogen atoms include fluorine, chlorine, bromine and iodine atoms; usually the halogen atoms are bromine and chlorine atoms.

Specific examples of such single ring Ar moieties include the following:

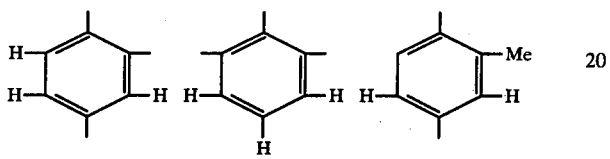

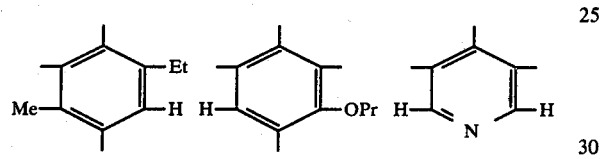

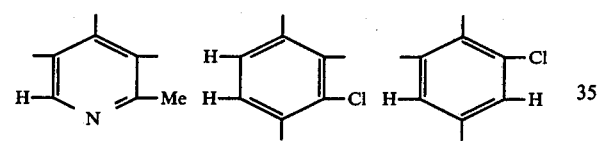

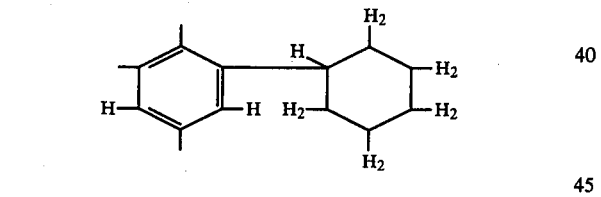

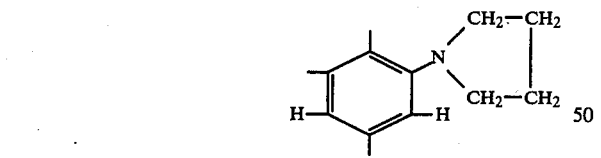

etc. wherein Me is methyl, Et is ethyl and Pr is n-propyl.

When Ar is a polynuclear fused-ring aromatic moiety, it can be represented by the general formula

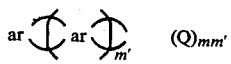 (Q)$_{mm'}$ wherein ar, Q and m are as defined hereinabove, m' is 1 to 4 and ⌒ represent a pair of fusing bonds fusing two rings so as to make two carbon atoms part of the rings of each of two adjacent rings. Specific examples of fused ring aromatic moieties Ar are:

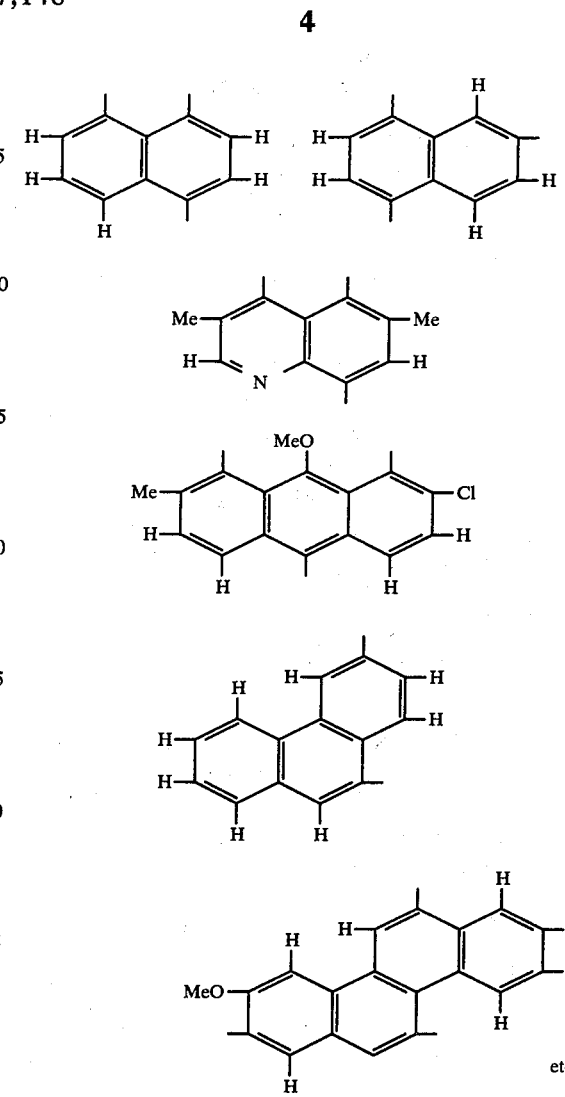

etc.

When the aromatic moiety Ar is a linked polynuclear aromatic moiety it can be represented by the general formula

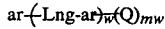

ar-(-Lng-ar)$_w$-(Q)$_{mw}$ wherein w is an integer of 1 to about 20, ar is as described above with the proviso that there are at least 3 unsatisfied (i.e., free) valences in the total of ar groups, Q and m are as defined hereinbefore, and each Lng is a bridging linkage individually chosen from the group consisting of carbon-to-carbon single bonds, ether linkages (e.g., —O—), keto linkages

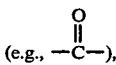

sulfide linkages (e.g., —S—), polysulfide linkages of 2 to 6 sulfur atoms (e.g., —S$_{2-6}$—), sulfinyl linkages (e.g., —S(O)—), sulfonyl linkages (e.g., —S(O)$_2$), alkylene linkages

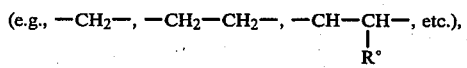

alkylidene linkages (e.g., —CR₂°—), alkylene ether linkages (e.g., —CH₂O—, —CH₂O—CH₂—, —CH₂—CH₂O—, —CH₂CH₂—OCH₂CH₂—, —CH₂CHOCH₂CH—
                                |       |
                                R°      R°

—CH₂CHOCHCH₂—, etc.),
     |      |
     R°     R° alkylene keto linkages (e.g., —CH₂C—, —CH₂CCH₂—),
          ‖          ‖
          O          O alkylene sulfide linkages (e.g., wherein one or more —O—'s in the alkylene ether linkages is replaced with an —S— atom), alkylene polysulfide linkages (e.g., wherein one or more —O—'s is replaced with a —S-2-6— group), amino linkages (e.g., —N—, —CH₂N—, —CH₂NCH₂—, —alk—N—, where alk is alkylene, etc.), and polyamine linkages (e.g., —N(alkN)$_{1-10}$, where the unsatisfied free N valences are taken up with H atoms or R° groups), each R° being a lower alkyl group.

Specific examples of Ar when it is a linked polynuclear aromatic moiety include:

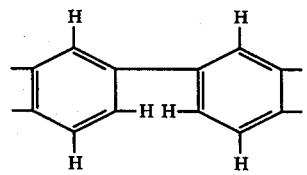

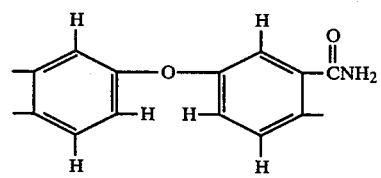

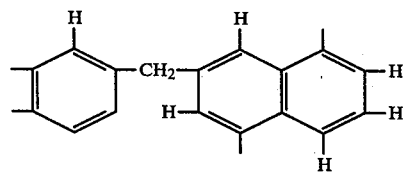

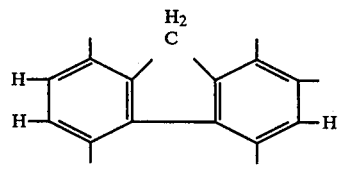

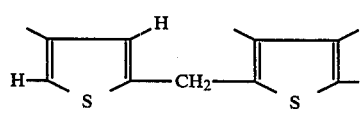

-continued

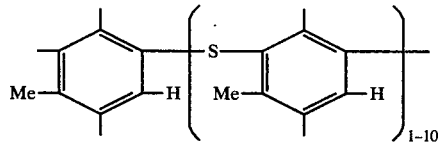

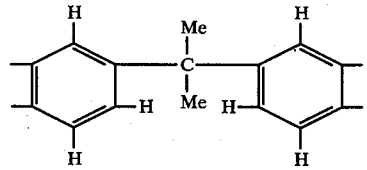

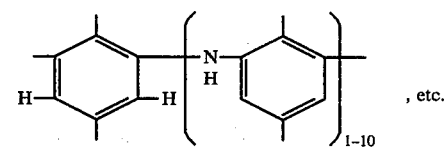, etc.

Usually all these Ar moieties are unsubstituted except for the R, —OH and —NO₂ groups (and any bridging groups).

For such reasons as cost, availability, performance, etc., the Ar moiety is normally a benzene nucleus, lower alkylene bridged benzene nucleus, or a naphthalene nucleus. Thus, a typical Ar moiety is a benzene or naphthalene nucleus having 3 to 5 unsatisfied valences, so that one or two of said valences may be satisfied by a hydroxyl group with the remaining unsatisfied valences being, insofar as possible, either ortho or para to a hydroxyl group. Usually Ar is a benzene nucleus having 3 to 4 unsatisfied valences so that one can be satisfied by a hydroxyl group with the remaining 2 or 3 being either ortho or para to the hydroxyl group.

The Aliphatic Substituent, R

The nitro phenols of the present invention contain, directly bonded to the aromatic moiety Ar, an aliphatic substituent R of at least about 40 carbon atoms. This R group can have up to about 500 carbon atoms. More than one such group can be present, but usually, no more than 2 or 3 such groups are present for each aromatic nucleus in the aromatic moiety Ar. Often, but not necessarily, there is one R group for each aromatic moiety. The total number of R groups present is indicated by the value for "a" in Formula I. Usually the R group has at least about 50 carbon atoms and up to about 400, more typically, up to about 300 carbon atoms. At least one of the R groups is in a position ortho or para to at least one —OH substituent attached directly to Ar. Typically when only one R group and —OH substituent are present per aromatic moiety Ar, the R group is para to the —OH substituent. Usually the aliphatic substituent R is hydrocarbyl in nature; it can, however, be substantially hydrocarbyl in nature and contain, in addition to carbon and hydrogen, up to about 10 weight percent other elements such as oxygen (usually in the form of ether or hydroxyl groups), sulfur (usually in the form of sulfide or thiol groups), and halogens (particularly chlorine and bromine). The R group is substantially saturated which means it can contain up to 1 carbon-to-carbon double bond per every 10 carbon-to-carbon single bonds. Preferably, however, R is saturated.

Generally the aliphatic R substituents are made from homo- or interpolymers (e.g., copolymers, terpolymers) of mono- and di-olefins having 2 to 10 carbon atoms, such as ethylene, propylene, butene-1, isobutene, butadiene, isoprene, 1-hexene, 1-octene, etc. Typically, these olefins are aliphatic hydrocarbon 1-monoolefins. A preferred source of the substituent R is poly(butene) obtained by polymerization of a $C_4$ refinery stream having a total butene content of 30 to 75 weight percent and isobutene content of 20 to 60 weight percent in the presence of a Lewis acid catalyst such as aluminum trichloride or boron trifluoride. These polybutenes contain predominantly (greater than 80% of total repeat units) isobutene repeating units of the configuration

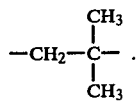

The attachment of the aliphatic R substituent to the aromatic moiety Ar of the nitro phenols of this invention can be accomplished by a number of techniques well known to skilled workers in the art. A particularly suitable technique is the Friedel-Crafts reaction, wherein an olefin (e.g., a polymer containing an olefinic bond), or halogenated or hydrohalogenated analog thereof, is reacted with a phenol. The reaction occurs in the presence of a Lewis acid catalyst (e.g., boron trifluoride and its complexes with ethers, phenols, hydrogen fluoride, etc.; aluminum chloride, aluminum bromide, zinc dichloride, etc.). Methods and conditions for carrying out these reactions are well known; see, for example, the discussion in the article entitled, "Alkylation of Phenols" in Kirk-Othmer Encyclopedia of Chemical Technology, Second Edition, Vol. 1, pages 894–895, Interscience Publishers, a division of John Wiley and Company, N.Y., 1963. Other equally appropriate and convenient techniques for attaching the aliphatic R substituent to the aromatic moiety Ar will occur readily to those skilled in the art.

As will be appreciated from inspection of Formula I the nitro phenols of this invention contain at least one of each of the following substituents: a hydroxyl group, a R group as defined above, and a nitro group, $-NO_2$. Each of the foregoing groups must be attached to a carbon atom which is a part of an aromatic nucleus in the Ar moiety. They need not, however, each be attached to the same aromatic ring if more than one aromatic nucleus is present in the Ar moiety.

In a preferred embodiment, the nitro phenols of this invention contain 1 or 2 each of the foregoing substituents and but a single aromatic ring, most preferably a benzene ring. This preferred class of nitro phenols can be represented by the formula

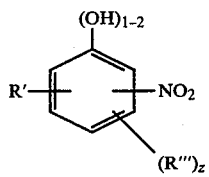

Formula II wherein R' is an aliphatic substituent having an average of from about 40 to about 500, usually about 50 to about 300 carbon atoms in a position ortho or para to a hydroxyl group; R''' is a member selected from the group consisting of lower alkyl, lower alkoxyl, nitro, halo, carboxy, carboxy ester of mono- and dihydric $C_{1-7}$ alkanols and carboxamide wherein the amide nitrogen can have up to 1 or 2 $C_{1-7}$ alkyl substituents; and z is 0 or 1. The substituent R' is of the same general character as R and the discussion of the character of R applies equally to R'. Usually R' is an alkyl or alkenyl substituent and z is 0. When R''' is present, it is often a nitro group and the nitro phenol is a dinitro phenol.

In a still more preferred embodiment of this invention, the nitro phenol is of the formula

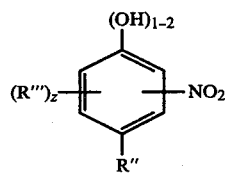

Formula III wherein R'' is an alkyl or alkenyl group derived from homopolymerized or interpolymerized $C_{2-10}$ 1-olefins located para to an $-OH$ group and has an average of from about 50 to about 300 carbon atoms; R''' is selected from the group consisting of lower alkyl, lower alkoxyl, nitro, and halo; and z is 0 or 1.

Usually R'' is derived from polymerized ethylene, propylene, butylene and mixtures thereof. Typically, it is derived from polymerized propylene or butylenes. In one embodiment z is 0; in another embodiment z is 1, R''' is nitro, only one $-OH$ group is present and the nitro group, R''', is located ortho to it.

The nitro phenols of the present invention can be prepared by a number of synthetic routes. These routes can vary in the type reactions used and the sequence in which they are employed. For example, an aromatic hydrocarbon, such as benzene, can be alkylated with alkylating agent such as a polymeric olefin to form an alkylated aromatic intermediate. This intermediate can then be nitrated, for example, to form polynitro intermediate and one of the nitro groups in this intermediate converted to a hydroxyl group through fusion with caustic to provide the desired nitro phenol.

Another useful route to the nitro phenols of this invention involves the alkylation of a phenol with an olefinic alkylating agent to form an alkylated phenol. This alkylated phenol can then be nitrated to form a nitro phenol.

Techniques for alkylating phenols are well known to those skilled in the art as the above-noted article in Kirk-Othmer Encyclopedia of Chemical Technology demonstrates. Techniques for nitrating phenols are also well known. See, for example, in Kirk-Othmer Encyclopedia of Chemical Technology, Second Edition, Vol. 13, the article entitled "Nitrophenols", page 888 et seq., as well as the treatises "Aromatic Substitution; Nitration and Halogenation" by P. B. D. De La Mare and J. H. Ridd, N.Y., Academic Press, 1959; "Nitration and Aromatic Reactivity" by J. G. Hogget, London, Cambridge University Press, 1961; and "The Chemistry of the Nitro and Nitroso Groups", Henry Feuer, Editor, Interscience Publishers, N.Y., 1969.

Aromatic hydroxy compounds can be nitrated with nitric acid, mixtures of nitric acid with acids such as sulfuric acid or boron trifluoride, $NO_2$, $N_2O_3$, $N_2O_4$, $N_2O_5$, $NO_2Cl$, $NO_2Br$, mixtures of alkali and alkaline earth metal nitrates with mineral acids (e.g., $H_2SO_4$), alkanoyl nitrates (e.g., acetyl nitrate) and mixtures of two or more of these nitrating agents. Generally nitric acid of a concentration of, for example, about 30–90% is a convenient nitrating reagent. Substantially inert liquid diluents such as acetic or butyric acid can aid in carrying out the reaction by improving reagent contact and heat transfer properties.

Conditions and procedures for nitrating hydroxy aromatic compounds are well known in the art. For example, the reaction can be carried out at temperatures of about −15° C. to about 150° C. Usually nitration of alkyl phenols is conveniently carried out between about 25°–75° C.

Generally, depending on the particular nitrating agent, about 0.5–4 moles of nitrating agent is used for every mole of aromatic nucleus present in the hydroxy aromatic intermediate to be nitrated. If more than one aromatic nucleus is present in the Ar moiety, the amount of nitrating agent can be increased proportionately according to the number of such nuclei present. For example, a mole of naphthalene-based aromatic intermediate has, for purposes of this disclosure, the equivalent of two "single ring" aromatic nuclei so that about 1–4 moles of nitrating agent would generally be used. When nitric acid is used as a nitrating agent usually about 1.0 to about 3.0 moles per mole of aromatic nucleus is used. Up to about a 5-molar excess of nitrating agent (per "single ring" aromatic nucleus) may be used when it is desired to drive the reaction forward or carry it out rapidly.

Nitration of a hydroxy aromatic intermediate generally takes 0.25 to 24 hours, though it may be convenient to react the nitration mixture for longer periods, such as 96 hours.

The typical route to the nitro phenols of this invention just described can be summarized as nitrating with at least one nitrating agent at least one phenol of the formula $(R)_a Ar'(OH)_c$ wherein each R is an aliphatic substituent of at least about 40, typically about 50 to about 300, carbon atoms; at least one R is in a position ortho or para to at least one —OH substituent attached directly to Ar'; a and c are each independently integers of 1 up to three times the number of aromatic nuclei in Ar', their sum not exceeding the number of unsatisfied valences in Ar', and Ar' is an aromatic moiety having at least one hydrogen bonded to a carbon of an aromatic ring and 0 to 3 optional substituents selected from the group consisting of lower alkyl, lower alkoxyl, halo, nitro, carboxy, carboxy ester of mono- and dihydric $C_{1-7}$ alkanols and carboxamide wherein the amide nitrogen can have up to 1 or 2 $C_{1-7}$ alkyl substituents and combinations of said optional substituents. In other respects Ar' is the same as Ar and the description of the latter given hereinabove applies equally to Ar'. Usually Ar' is a benzene nucleus and R has an average of up to about 500 carbons and typically is derived from homopolymerized or interpolymerized $C_{2-10}$ olefins and mixtures thereof.

Typically, such nitrated phenols are made by nitrating with a nitrating agent at least one compound of the formula

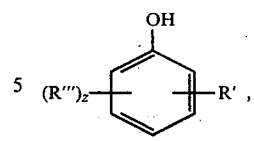

Formula IV wherein R' and R''' are as described hereinabove and R' is located in a position ortho or para to the hydroxyl group; and z is 0 or 1. Typically R' is para to the hydroxyl group and z is 0.

Certain nitrophenols within the scope of this invention having linked aromatic nuclei can be made by several alternative synthetic sequences. For example, a hydrocarbon-substituted phenolic compound such as those described hereinabove can be first reacted with a linking reagent such as an aldehyde or ketone (e.g., formaldehyde) to form a linked product having, for example, methylene linkages between aromatic nuclei. These linked intermediates can then be nitrated by the procedures described hereinabove to give the desired linked nitrophenol. Such a sequence can be illustrated by the following sequence:

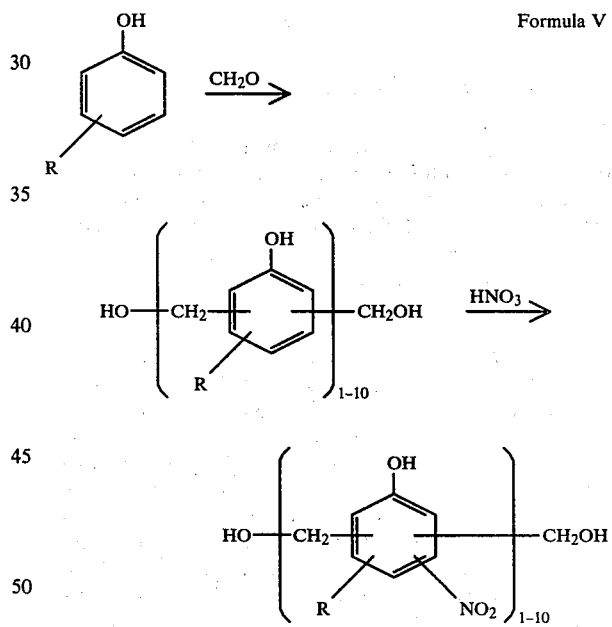

Formula V

Alternatively, a nitrophenol with a single ring or fused multi-ring aromatic moiety made, for example, as described hereinabove, can be reacted with the linking reagent such as aldehyde, formaldehyde to give the desired linked nitro phenol. This sequence can be illustrated by the following sequence:

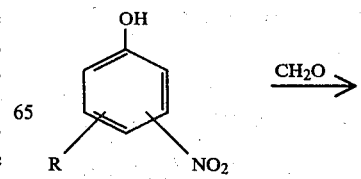

Formula VI

-continued

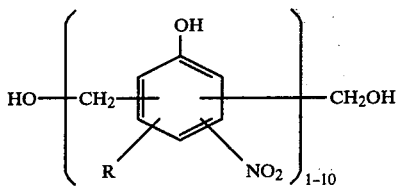

Still another route to linked nitrophenols within the scope of this invention having linked aromatic nuclei is through the condensation of a hydrocarbon-substituted phenol and a nitrophenol which can or cannot be hydrocarbon-substituted with the aid of a linking agent such as sulfur, formaldehyde, etc. This sequence can be illustrated by the sequence:

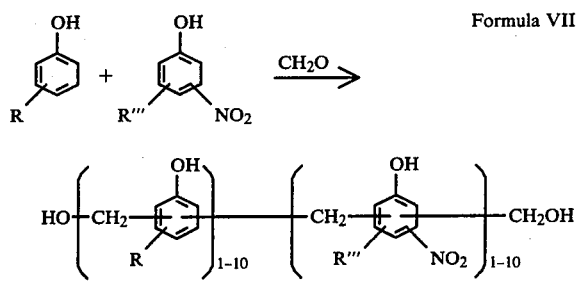

Formula VII

R and R''' in Formulae V-VII are as described hereinabove.

The following examples demonstrate the practice of the present invention in some of its various aspects. All parts and percentages in the examples and elsewhere in the specification and claims are by weight and likewise, all temperatures are in degrees Celsius (°C.), unless expressly stated to the contrary.

EXAMPLE 1

A mixture of 1750 parts of polybutene-substituted phenol (having an average of about 75 carbons in the polybutene substituent) and 1288 parts diluent mineral oil is heated under nitrogen to 60°. Heating is stopped and concentrated nitric acid (70%, 126 pbw) is added slowing over 1.25 hours so as to maintain the temperature at 59°-60°. The nitric acid-containing mixture is then stirred at 57°-60° for 1.5 hours. Aqueous material is then removed as a distillate with the aid of a Dean Stark trap as the mixture is heated to 140°. The residual mixture is an oil solution of the desired product and exhibits the expected infrared bands at 6.5 microns and 7.6 microns indicative of the nitro group.

EXAMPLE 2

An alkylated phenol is prepared by reacting phenol with polyisobutene having a number average molecular weight of approximately 1000 (vapor phase osmometry) in the presence of a boron trifluoride phenol complex catalyst. Stripping of the product thus formed first to 230°/760 torr (vapor temperature) and then to 205° vapor temperature/50 torr provides purified alkylated phenol.

To a mixture of 265 parts of purified alkyl phenol, 176 parts blend oil and 42 parts of a petroleum naphtha is added slowly to a mixture of 18.4 parts of concentrated nitric acid (69-70%) and 35 parts of water. The reaction mixture is stirred for 3 hours at about 30°-45°, stripped to 120°/20 torr and filtered to provide an oil solution of the desired nitro phenol.

EXAMPLE 3

To a mixture of 400 parts of polyisobutene-substituted phenol (wherein the polyisobutene substituent contains an average of approximately 100 carbon atoms), 125 parts of textile spirits and 266 parts of a diluent mineral oil at 28° is slowly added 22.8 parts of nitric acid (70%) in 50 parts of water over a period of 0.33 hour. The mixture is stirred at 28°-34° for 2 hours and stripped to 158°/30 torr. Filtration provides an oil solution (40%) of the desired nitro phenol having a nitrogen content of 0.88%.

EXAMPLE 4A

A mixture of 2,160 parts of the polyisobutene-substituted phenol of Example 3A and 1,440 parts of a diluent mineral oil is heated to 60°. Then 25 parts of paraformaldehyde is added to the mixture followed by 15 parts of aqueous hydrochloric acid. The mixture is heated to 115° for 1 hour. After storage for 16 hours at room temperature the reaction mixture is heated to 160° for 1 hour while 20 parts of distillate are removed. Stripping of the reaction mixture to 160°/15 torr provides an oil solution of the desired methylene-linked, polyisobutene-substituted phenol.

EXAMPLE 4B

To 2,406 parts of the oil solution described in Example 4A and 600 parts of textile spirits is added 90 parts nitric acid (70%) over 1.5 hours. The reaction mixture is stirred for 1.5 hours, stored for 63 hours at room temperature and then heated for 8 hours at 90°. Stripping to 160°/18 torr provides an oil solution of the desired nitrated linked phenol containing 0.79% nitrogen.

EXAMPLE 5

A mixture of 1,962 parts of the polyisobutene-substituted phenol of Example 2, 49.5 parts of paraformaldehyde, 15 parts of aqueous hydrochloric acid and 1,372 parts of diluent mineral oil is heated for 7 hours at 115°. The reaction temperature is then increased to 160°-165° and held there for an additional 7 hours. Four hundred parts of textile spirits is added to the mixture and it is cooled to 30°. Then 137 parts of nitric acid (70%) in 140 parts of water is slowly added. The reaction mixture is stirred for 1.5 hours at 30°-35° and then stripped to 170°/28 torr to provide an oil solution of the nitro phenol which is clarified by filtration.

EXAMPLE 6

To a mixture of 654 parts of the polyisobutene-substituted phenol of Example 2 and 654 parts of isobutyric acid at 27° to 31°, is added 90 parts of 16 molar nitric acid over a period of 0.5 hour. The reaction mixture is held at 50° for 3 hours and then stored at room temperature for 63 hours. Stripping to 160°/26 torr and filtration through filter aid provides the desired dinitro phenol which has a nitrogen content of 1.8%.

EXAMPLE 7

A mixture of 4,578 parts of the polyisobutene-substituted phenol of Example 2, 3,052 parts of diluent mineral oil and 725 parts of textile spirits is heated to 60° to achieve homogenity. After cooling to 30°, 319.5 parts of 16 molar nitric acid in 600 parts of water is added to the mixture. Cooling is necessary to keep the mixture below 40°. After stirring the reaction mixture for an additional 2 hours, 3,710 parts is transferred to a second reaction vessel. This 3,710 parts is treated with an additional 127.8 parts of 16 molar nitric acid in 130 parts of water at 25°-30°. The reaction mixture is stirred for 1.5 hours and then stripped to 220°/30 torr. Filtration provides an oil solution of the dinitro phenol.

The nitrations in examples 8-14 are carried out in essentially the same manner described in Example 1, using the hydroxy aromatic compounds and amounts of nitric acid indicated in Table A.

TABLE A

| EXAMPLE | HYDROXY AROMATIC COMPOUND | | |
|---|---|---|---|
| | Name | Mol. Wt.[1] | MOLES HNO$_3$[2] |
| 8 | 2,2'dipoly(isobutene)yl-4,4'-dihydroxy biphenyl | 2500 | 2.2 |
| 9 | 8-hydroxy-2-poly(propene)yl-1-azanaphthalene | 900 | 1.0 |
| 10 | 4-poly(isobutene)yl-1-naphthol | 1700 | 1.1 |
| 11 | 2-poly(propene/butene-1)yl-4,4'-isopropylidene-bisphenol[3] | 3200 | 2.4 |
| 12 | 4-poly(isobutene)yl-3-hydroxy pyridine | 1300 | 1.0 |

[1]Number average molecular weight by vapor phase osmometry
[2]Moles of HNO$_3$ per mole of "single ring" aromatic nucleus
[3]The molar ratio of propene to butene-1 in the substituent is 2:3

EXAMPLE 13

A mixture of 960 parts polybutene-substituted phenol ($\overline{M}n$ 1340, VPO), 705 parts mineral oil, 40 parts butyl alcohol, 4.8 parts sodium hydroxide and 39.6 parts paraformaldehyde, is heated at 82°-87° for three hours. The mixture is then neutralized with 3.6 parts glacial acetic acid. Distillate is removed as the mixture is heated to 125° C.; 83.4 parts of ortho-nitrophenol is then added and the mixture is heated at 175° to 185° for three hours. Stripping of the mixture at 190°-200° under vacuum and filtration provides the desired reaction product in an oil solution containing 40% by weight mineral oil. This solution has a nitrogen content of 0.24%.

EXAMPLE 14

A mixture of 640 parts of a polybutene-substituted phenol ($\overline{M}n$ 1600, VPO) made in essentially the same fashion described in Example 2, 33 parts paraformaldehyde, 10 parts aqueous concentrated hydrochloric acid, 10 parts water and 1500 parts petroleum solvent is heated at reflux (70°-95°) for 22 hours. The petroleum solvent is stripped off and residual mixture heated to 225° for an additional 21 hours. The residue is then diluted with 1600 parts n-hexane, cooled with an ice bath, and treated with a mixture of 93.5 parts concentrated nitric acid and 90 parts water over 5 hours. After stirring for an additional 4.5 hours at room temperature, the reaction mixture is stripped to 150°/26 torr. Diluent lubricating oil (1,069 parts) is added, and the reaction mixture was filtered to provide an oil solution containing 40% diluent oil of the desired product. This solution has a nitrogen content of 0.8%.

EXAMPLE 15

To a mixture of 825 parts of the oil solution of nitro phenol described in Example 2, and 3 parts of the concentrated aqueous sodium hydroxide is added 14 parts of paraformaldehyde. This mixture is heated at 80° for 3.5 hours. The reaction temperature is then decreased to 50° and the mixture neutralized with 3.5 parts of glacial acetic acid. Filtration provides an oil solution of the desired product containing 39% mineral oil.

EXAMPLE 16

To 1000 parts of the nitro phenol described in Example 1, is added 41 parts sulfur dichloride. The addition is carried out at 18°-24° for 0.6 hour and the reaction mixture contains a small piece of metallic iron. The mixture is heated at 35°-70° for 5.5 hours. The provision is then made for blowing a slow stream of nitrogen through the stirred mixture and it is heated under this condition for a total of 7 hours at a temperature ranging between 120°-160°. Provision is made during the heating step to collect the gaseous hydrochloric acid evolved during the reaction in a water trap. Filtration of the residual mixture through filter aid provides the desired product which contains 1.5% sulfur.

EXAMPLE 17

A polybutene-substituted potassium phenate (molecular weight 1000, VPO), is carboxylated by treating an oil solution thereof with carbon dioxide at 150° C. The resulting mixture is acidified with aqueous hydrochloric acid and treated with ethylene oxide to form the beta-hydroxyethyl ester. To a mixture of 517 parts of this polybutene substituted beta-hydroxyethyl salicylate and 90 parts of petroleum naphtha is added 32 parts of concentrated nitric acid. The addition is carried out at room temperature over a period of one hour at a temperature of 20°-30°. The mixture is then stirred for two hours at room temperature and heated at 120° for an additional two hours. Filtration through filter aid provides an oil solution of the desired nitrated polybutene-substituted salicylate ester containing 0.6% nitrogen.

As previously indicated, the nitro phenols of this invention are useful as additives in preparing lubricant compositions where they function as detergents, dispersants and demulsifiers.

The lubricating oil compositions of this invention are based on natural and synthetic lubricating oils and mixtures thereof. These lubricants include crankcase lubricating oils for spark-ignited and compression-ignited internal combustion engines, such as Otto cycle and 2-cycle (2-stroke) automobile and truck engines, marine and railroad diesel engines, and the like. For the purpose of this description Wankel engines are considered to be of the 2-cycle type. Automatic transmission fluids, transaxle lubricants, gear lubricants, industrial oils such as metal-working lubricants, hydraulic fluids and other lubricating oil and grease compositions can also benefit from the incorporation therein of the nitro phenols of the present invention.

Natural oils include animal oils and vegetable oils (e.g., castor oil, lard oil) as well as mineral lubricating oils such as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. Synthetic lubricating oils include hydrocarbon oils and halo-substituted hydrocarbon oils such as homopolymerized and interpolymerized olefins (e.g., polybutylenes, polypropylenes, propylene-isobutylene copolymers, chlorinated polybutylenes, etc.); poly(1-hexenes, poly(1-octenes), poly(1-decenes), etc. and mixtures thereof; alkylbenzenes (e.g., dodecylbenzenes, tetradecylbenzenes, dinonylbenzenes, di-(2-ethylhexyl)-benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like.

Alkylene oxide homopolymers and interpolymers and derivatives thereof where the terminal hydroxyl groups have been modified by esterification, etherification, etc., constitute another class of known synthetic lubricating oils. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$ Oxo acid diester of tetraethylene glycol.

Another suitable class of synthetic lubricating oils comprises the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_5$ to $C_{12}$ monocarboxylic acids and polyols and polyol ethers such as neopentyl glycol, trimethylol propane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl)silicate, tetra-(4-methylhexyl)silicate, tetra(p-tert-butylphenyl)silicate, hexyl-(4-methyl-2-pentoxy)disiloxane, poly(methyl)siloxanes, poly(methylphenyl)siloxanes, etc.). Other synthetic lubricating oils include liquid esters of phosphorus-containing acids (e.g., tricresyl phosphate, trioctyl phosphate, diethyl ester of decane phosphonic acid, etc.), polymeric tetrahydrofurans and the like.

Unrefined, refined and rerefined oils, either natural or synthetic (as well as mixtures of two or more of any of these) of the type disclosed hereinabove can be used in the lubricant composition of the present invention. Unrefined oils are those obtained directly from a natural or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, secondary distillation, acid or base extraction, filtration, percolation, etc. Rerefined oils are obtained by processes, similar to those used to obtain refined oils, applied to refined oils which have been already used in service. Such rerefined oils are also known as reclaimed or reprocessed oils and often are additionally processed by techniques directed to removal of spent additives and oil breakdown products.

In general, about 0.05–30, usually about 0.1–15 parts (by weight) of at least one nitro phenol of this invention is dissolved or stably dispersed in 100 parts of oil to produce a satisfactory lubricant. The invention also contemplates the use of other additives in combination with the composition of this invention. Such additives include, for example, auxiliary detergents and dispersants of the ashproducing or ashless type, oxidation-inhibiting agents, pour point depressing agents, extreme pressure agents, color stabilizers and anti-foam agents.

The term "stably dispersed" as used in this specification and appended claims is intended to mean a composition (e.g., a single additive or compound, a mixture of two or more additives or compounds, etc.) is capable of being dispersed in a given medium to an extent which allows it to function in its intended manner. Thus, for example, where a composition of this invention is used in an oil, it is sufficient that the composition be capable of being suspended in the oil in an amount sufficient to enable the oil to possess one or more of the desired properties imparted to it by the suspended composition. Such suspension of the compositions can be achieved in various conventional ways. For example, in constantly circulating oil or oil in splash lubricating systems, physical agitation can keep the compositions suspended in oil. Likewise, conventional dispersants (such as the acylated nitrogen dispersants disclosed in U.S. Pat. No. 3,219,666) often found in lubricating oils and fuels promote the stable dispersion or suspension of the composition. In any event, the intended compositions will be "soluble" or "stably dispersible" in the normally liquid media in which they will be used in at least the minimum concentrations set forth elsewhere herein. Thus, the terminology "soluble" and "stably dispersible" is used in a conventional manner and will be understood to those of ordinary skill in the art.

As used in the specification and the appended claims, the term "substantially inert" when used to refer to solvents, diluents, base stocks, and the like, is intended to mean that the solvent, diluent, etc., is inert to chemical or physical change under the conditions in which it is used so as not to materially interfere in an adverse manner with the preparation, storage, blending and/or functioning of the compositions, additive, compound, etc. of this invention in the context of its intended use. For example, small amounts of a solvent, diluent, etc. can undergo minimal reaction or degradation without preventing the making and using of the invention as described herein. In other words, such reaction or degradation, while technically discernible, would not be sufficient to deter the practical worker of ordinary skill in the art from making and using the invention for its intended purposes. "Substantially inert" as used herein is, thus, readily understood and appreciated by those of ordinary skill in the art.

The nitro phenols of this invention can also be used in fuels where they function as detergent/dispersants, antioxidants and demulsifying agents. Fuel compositions of this invention usually contain a major portion of a normally liquid fuel such as hydrocarbonaceous petroleum distillate fuel (e.g., motor gasoline as defined by ASTM Specification D-439-73 and diesel fuel or fuel oil as defined by ASTM Specification D-396). Normally liquid fuel compositions comprising non-hydrocarbonaceous materials such as alcohols, ethers, organo-nitro compounds and the like (e.g., methanol, ethanol, diethyl ether, methyl ethyl ether, nitromethane) are also within the scope of this invention as are liquid fuels derived from vegetable or mineral sources such as corn, alfalfa, shale, and coal. Normally liquid fuels which are mixtures of one or more hydrocarbonaceous fuel and one or more non-hydrocarbonaceous material are also contemplated. Examples of such mixtures are combinations of gasoline and ethanol, diesel fuel and ether, gasoline and nitromethane, etc. Particularly preferred is gasoline, that is, a mixture of hydrocarbons having an ASTM boiling point of 60° C., at the 10% distillation point to about 205° C. at the 90% distillation point.

Generally, these fuel compositions contain an amount of at least one nitro phenol of this invention sufficient to impart dispersant, detergent or demulsifying properties to the fuel; usually this amount is about 1 to about 10,000, preferably 4 to 1,000, parts by weight of the reaction product per million parts by weight of fuel. Preferred are gasoline-based fuel compositions which exhibit engine sludge dispersancy and detergency and carburetor detergency properties.

The fuel compositions of this invention can contain, in addition to the compositions of this invention, other additives which are well known to those of skill in the art. These can include anti-knock agents such as tetraalkyl lead compounds, lead scavengers such as haloalkanes (e.g., ethylene dichloride and ethylene dibromide), deposit preventors or modifiers such as triaryl phosphates, dyes, cetane improvers, anti-oxidants such as 2,6-di-tertiary-butyl-4-methylphenol, rust inhibitors, such as alkylated succinic acids and anhydrides, bacteriostatic agents, gum inhibitors, metal deactivators, demulsifiers, upper cylinder lubricants, anti-icing agents and the like.

In certain preferred fuel compositions of the present invention, the afore-described compositions of this invention are combined with other ashless dispersants in gasoline. Such ashless dispersants are preferably esters of a mono- or polyol and a high molecular weight mono-or polycarboxylic acid acylating agent containing at least 30 carbon atoms in the acyl moiety. Such esters are well known to those of skill in the art. See, for example, French Pat. No. 1,396,645; British Pat. Nos. 981,950 and 1,055,337; and U.S. Pat. Nos. 3,255,108; 3,311,558; 3,331,776; 3,346,354; 3,522,179; 3,579,450; 3,542,680; 3,381,022; 3,639,242; 3,697,428; 3,708,522; and British Patent Specification No. 1,306,529. These patents are expressly incorporated herein by reference for their disclosure of suitable esters and methods for their preparation. Generally, the weight ratio of the compositions of this invention to the aforesaid ashless dispersants is about 0.1 to about 10.0; preferably about 1 to about 10 parts of composition of this invention of 1 part ashless dispersant.

In still another embodiment of this invention, the inventive nitro phenols can be combined with Mannich condensation products formed from substituted phenols, aldehydes, polyamines, and amino pyridines to make lubricants and/or fuel additives. Such condensation products are described in U.S. Pat. Nos. 3,649,659; 3,558,743; 3,539,633; 3,704,308; and 3,724,277.

The nitro phenols of this invention can be added directly to the fuel or lubricating oil to form the fuel and lubricant compositions of this invention or they can be diluted with at least one substantially inert, normally liquid organic solvent/diluent such as mineral oil, xylene, or a normally liquid fuel as described above, to form an additive concentrate which is then added to the fuel or lubricating oil in sufficient amounts to form the inventive fuel and lubricant composition described herein. These concentrates generally contain about 30 to about 90 percent of the composition of this invention and can contain in addition any of the above-described conventional additives, particularly the afore-described ashless dispersants in the aforesaid proportions. The remainder of the concentrate is the solvent/diluent.

This invention also includes two-cycle engine lubricating oils containing the hereinbefore described nitro phenols.

In general, these two-cycle engine lubricating oil compositions contain about 98 to about 55% oil or mixture of oils of lubricating viscosity. Typical compositions contain about 90 to about 70% oil. The presently preferred oils are mineral oils and mineral oil-synthetic polymer and/or ester oil mixtures. Oily polybutene fractions of molecular weights of about 250 to about 1,000 (as measured by vapor phase osmometry) and fatty acid ester oils of polyols such as pentaerythritol and trimethylol propane are typical useful synthetic oils.

These oil compositions contain about 2 to about 30%, typically about 5 to about 20%, of at least one nitro phenol as described hereinbefore. Other additives such as auxiliary detergents and dispersants of the ash-producing or ashless type, anti-oxidants, coupling agents, pour point depressing agents, extreme pressure agents, color stabilizers and anti-foam agents can also be present.

Detergent-dispersants of ashless types and ash-producing metallic types are used to control piston ring sticking and general engine cleanliness. Heavy duty twocycle lubricants require the use of suitable ashless dispersants because ash-forming detergents tend to form combustion chamber deposits which induce preignition. Other formulations for use in less severe service can contain calcium, barium or magnesium sulfonates either singly, in combination with one another, or in combination with ashless dispersants. Anti-oxidants can be included to promote lubricant thermal stability.

Polymeric VI improvers have been and are being used in two-cycle oils to improve lubricant film strength and engine cleanliness. Dye may be used for identification purposes and to indicate whether a two-cycle fuel mix contains lubricant. Coupling agents are incorporated into some products to provide better component solubilities and improved fuel/lubricant mix water tolerance.

Anti-wear and lubricity improvers, particularly sulfurized sperm oil and sulfurized sperm oil substitutes and other fatty acid and vegetable oils, such as castor oil, are used in two-cycle engine oils for special applications, such as racing and for very high fuel/lubricant ratios. Scavengers or combustion chamber deposit modifiers are sometimes used to promote better spark plug life and to remove carbon deposits. Halogenated compounds and/or phosphorous-containing materials may be used for this application.

Rust and corrosion inhibitors of all types are and may be incorporated into two-cycle oil formulations. Odorants or deodorants are sometimes used for aesthetic reasons.

Lubricity agents such as synthetic polymers, (e.g., polyisobutene having a number average molecular weight in the range of about 750 to about 15,000, as measured by vapor phase osmometry or gel permeation chromatography), polyol ether (e.g., poly(oxyethyleneoxypropylene)ethers) and ester oils (e.g., the ester oils described above) can also be used in the two-cycle engine oil compositions of this invention. Natural oil fractions such as bright stocks (the relatively viscous products formed during conventional lubricating oil manufacture from petroleum) can also be used for this purpose. They are usually present in the two-cycle oil in the amount of about 3 to about 20% of the total oil composition.

The two-cycle engine oils of this invention can also contain auxiliary detergent-dispersants. Typical examples are the amide, amine salt and/or amidine products formed by reaction of fatty acids of 5 to about 22 carbon atoms (e.g., isostearic acid and mixtures of isostearic and stearic acid) with an alkylene polyamine of 2 to about 10 amino groups and 2 to about 20 carbon atoms, such as ethylene diamine, diethylene triamine, triethylene tetramine, tetraethylene pentamine, etc., including commercially available mixtures of such alkylene polyamines. Such auxiliary detergent-dispersants are represented by those disclosed in U.S. Pat. No. 3,169,980 which is expressly incorporated herein by reference for such disclosure.

Diluents such as petroleum naphthas boiling at the range of about 38°-90° (e.g., Stoddard Solvent) can also be included in the oil compositions of this invention, typically in an amount of 5 to 25%.

An illustrative two-cycle engine oil lubricant composition contains 2-10% of one or more nitro phenols described hereinbefore such as that described in Example 1, and a base oil composed of about 70-80 parts by volume 650 neutral oil, 8-12 parts by volume bright stock and 10-20 parts by volume Stoddard Solvent.

As is well known to those skilled in the art, two-cycle engine lubricating oils can be added directly to the fuel to form a mixture of oil and fuel which is then introduced into the engine cylinder. Such lubricant-fuel oil mixtures are within the scope of this invention. Such lubricant-fuel blends generally contain per 1 part of oil about 15-250 parts fuel, typically they contain 1 part oil to about 50-100 parts fuel.

A typical example of the two-cycle engine oils of this invention is the following:

| Component | Percent (By Wt.) |
|---|---|
| Base Oil[1] | 60.0 |
| Bright Stock[2] | 10. |
| Stoddard Solvent | 15. |
| Nitro Phenol Additive[3] | 15. |

[1] A solvent-refined neutral oil having a viscosity of 650 SUS at 98.8° C.
[2] Having a viscosity of 150 SUS at 98.8° C.
[3] A mineral oil solution containing 60% of the nitro phenol prepared as described in Example 2.

The fuels used in two-cycle engines are well known to those skilled in the art and usually contain a major portion of a normally liquid fuel such as hydrocarbonaceous petroleum distillate fuel (e.g., motor gasoline as defined by ASTM Specification D-439-73). Such fuels can also contain non-hydrocarbonaceous materials such as alcohols, ethers, organo-nitro compounds and the like (e.g., methanol, ethanol, diethyl ether, methyl ethyl ether, nitromethane) are also within the scope of this invention as are liquid fuels derived from vegetable or mineral sources such as corn, alfalfa, shale and coal. Examples of such fuel mixtures are combinations of gasoline and ethanol, diesel fuel and ether, gasoline and nitromethane, etc. Particularly preferred is gasoline, that is, a mixture of hydrocarbons having an ASTM boiling point of 60° C. at the 10% distillation point to about 205° C. at the 90% distillation point.

Two-cycle engine fuels also contain other additives which are well known to those of skill in the art. These can include anti-knock agents such as tetra-alkyl lead compounds, lead scavengers such as halo-alkanes (e.g., ethylene dichloride and ethylene dibromide), deposit preventors or modifiers such as triaryl phosphates, dyes, cetane improvers, anti-oxidants such as 2,6-di-tertiarybutyl-4-methylphenol, rust inhibitors, such as alkylated succinic acids and anhydrides, bacteriostatic agents, gum inhibitors, metal deactivators, demulsifiers, upper cylinder lubricants, anti-icing agents and the like.

The nitro phenols of this invention are also useful as intermediates or precursors for conversion into other materials useful as fuel and lubricating oil additives. For example, reduction of the nitro group in these nitro phenols can lead to amino phenols useful in many such applications.

What is claimed is:

1. A nitro phenol of the formula

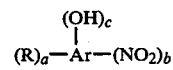

wherein R is an aliphatic substituent of at least about 40 carbon atoms; R is para to at least one -OH substituent attached directly to Ar; b and c are each independently integers of 1 up to three times the number of aromatic nuclei in Ar with the sum b+c not exceeding the number of unsatisfied valences in Ar, a is one and Ar is a benzene moiety having 0 to 3 optional substituents selected from the group consisting of lower alkyl, lower alkoxyl, halo, carboxy, carboxy ester of mono- and dihydric $C_{1-7}$ alkanols and carboxamide wherein the amide nitrogen can have up to 1 or 2 $C_{1-7}$ alkyl substituents and combinations of said optional substituents.

2. A nitro phenol as claimed in claim 1 wherein R has an average of up to about 500 carbon atoms.

3. A nitro phenol as claimed in claim 2 wherein R is a purely hydrocarbyl substituent.

4. A nitro phenol as claimed in claim 3 wherein R is alkyl or alkenyl.

5. A nitro phenol as claimed in claim 1 wherein R is a substituent of at least about 50 to about 300 carbon atoms.

6. A nitro phenol as claimed in claim 5 wherein R is made from homopolymerized or interpolymerized $C_{2-10}$ olefins.

7. A nitro phenol as claimed in claim 6 wherein said olefins are selected from the group consisting of $C_{2-10}$ 1-olefins and mixtures thereof.

8. A nitro phenol as claimed in claim 6 wherein said 1-olefins are selected from the group consisting of ethylene, propylene, butylenes, and mixtures thereof.

9. A nitro phenol as claimed in claim 1 wherein b and c are each 1.

10. A nitro phenol as claimed in claim 4 wherein R is derived from homopolymerized or interpolymerized $C_{2-10}$ 1-olefins.

11. A nitro phenol as claimed in claim 10 wherein said 1-olefins are selected from the group consisting of ethylene, propylene, butylenes, and mixtures thereof.

12. A nitro phenol of the formula

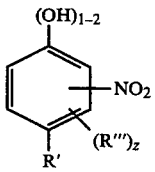

wherein R' is an aliphatic substituent having an average of from about 40 to about 500 carbon atoms in a position para to a hydroxyl group; R''' is a member selected from the group consisting of lower alkyl, lower alkoxyl, nitro, halo, carboxy, carboxy ester of mono- and dihydric $C_{1-7}$ alkanols and carboxamide wherein the amide nitrogen can have up to 1 or 2 $C_{1-7}$ alkyl substituents; and z is 0 or 1.

13. A nitro phenol as claimed in claim 12 wherein R' is hydrocarbyl and contains at least about 50 to about 300 carbon atoms.

14. A nitro phenol as claimed in claim 13 wherein R' is an alkenyl or alkyl group.

15. A nitro phenol as claimed in claim 12 wherein z is zero.

16. A nitro phenol as claimed in claim 15 wherein R' contains an average of at least about 50 to about 300 carbon atoms.

17. A nitro phenol as claimed in claim 12 wherein R' is a substituent derived from homopolymerized or interpolymerized $C_{2-10}$ olefins.

18. A nitro phenol as claimed in claim 17 wherein said $C_{2-10}$ olefins are selected from the group consisting of $C_{2-10}$ 1-olefins and mixtures thereof.

19. A nitro phenol as claimed in claim 18 wherein said 1-olefins are selected from the group consisting of ethylene, propylene, butylenes, and mixtures thereof.

20. A nitro phenol of the formula

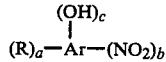

wherein R is an aliphatic substituent of at least about 40 carbon atoms; R is para to at least one —OH substituent attached directly to Ar; b and c are each independently integers of 1 up to three times the number of aromatic nuclei in Ar with the sum b+c not exceeding the number of unsatisfied valences in Ar, a is one and Ar is a benzene moiety having 0 to 3 optional substituents selected from the group consisting of lower alkyl or halo or combinations of said optional substituents.

21. A nitro phenol as claimed in claim 20 wherein R has an average of up to about 500 carbon atoms.

22. A nitro phenol as claimed in claim 21 wherein R is a purely hydrocarbyl substituent.

23. A nitro phenol as claimed in claim 22 wherein R is alkyl or alkenyl.

24. A nitro phenol as claimed in claim 20 wherein R is a substituent of at least about 50 to about 300 carbon atoms.

25. A nitro phenol as claimed in claim 24 wherein R is made from homopolymerized or interpolymerized $C_{2-10}$ olefins.

26. A nitro phenol as claimed in claim 25 wherein said olefins are selected from the group consisting of $C_{2-10}$ 1-olefins and mixtures thereof.

27. A nitro phenol as claimed in claim 25 wherein said 1-olefins are selected from the group consisting of ethylene, propylene, butylenes, and mixtures thereof.

28. A nitro phenol as claimed in claim 20 wherein b and c are each 1.

29. A nitro phenol as claimed in claim 60 wherein R is a substituent having an average of at least about 40 carbon atoms and is derived from homopolymerized or interpolymerized $C_{2-10}$ 1-olefins.

30. A nitro phenol as claimed in claim 29 wherein said 1-olefins are selected from the group consisting of ethylene, propylene, butylenes, and mixtures thereof.

31. A nitro phenol of the formula

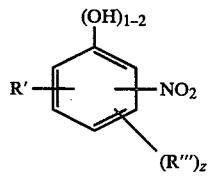

wherein R' is an aliphatic substituent having an average of from about 40 to about 500 carbon atoms in a position para to a hydroxyl group; R''' is a member selected from the group consisting of lower alkyl or halo; and z is 0 or 1.

32. A nitro phenol as claimed in claim 31 wherein R' is hydrocarbyl and contains at least about 50 to about 300 carbon atoms.

33. A nitro phenol as claimed in claim 32 wherein R' is an alkenyl or alkyl group.

34. A nitro phenol as claimed in claim 31 wherein z is zero.

35. A nitro phenol as claimed in claim 34 wherein R' contains an average of at least about 50 to about 300 carbon atoms.

36. A nitro phenol as claimed in claim 31 wherein R' is a substituent derived from homopolymerized or interpolymerized $C_{2-10}$ olefins.

37. A nitro phenol as claimed in claim 36 wherein said $C_{2-10}$ olefins are selected from the group consisting of $C_{2-10}$ 1-olefins and mixtures thereof.

38. A nitro phenol as claimed in claim 37 wherein said 1-olefins are selected from the group consisting of ethylene, propylene, butylenes, and mixtures thereof.

39. A nitrated phenol made by nitrating with at least one nitrating agent at least one phenol of the formula $(R)_a Ar'(OH)_c$ wherein R is an aliphatic substituent of at least about 40 carbon atoms; R is para to at least one —OH substituent attached directly to Ar'; c is one up to three times the number of aromatic nuclei in Ar', a is one and Ar' is a benzene moiety having 0 to 3 optional substituents selected from the group consisting of lower alkyl, lower alkoxyl, halo, nitro, carboxy, carboxy ester of mono- and dihydric $C_{1-7}$ alkanols and carboxamide wherein the amide nitrogen can have up to 1 or 2 $C_{1-7}$ alkyl substituents and combinations of said optional substituents.

40. A nitrated phenol as claimed in claim 39 wherein R has an average of up to about 500 carbon atoms.

41. A nitrated phenol as claimed in claim 39 wherein the nitrating agent is selected from the group consisting of nitric acid, $No_2$, $N_2O_3$, $N_2O_4$, $N_2O_5$, $NO_2Cl$, mixtures of alkali and alkaline earth metal nitrates with mineral acids, alkanoyl nitrates and mixtures thereof.

42. A nitrated phenol as claimed in claim 40 wherein R is hydrocarbyl and contains at least about 50 to about 300 carbon atoms.

43. A nitrated phenol as claimed in claim 32 wherein R is derived from homopolymerized or interpolymerized $C_{2-10}$ olefins and mixtures thereof.

44. A nitrated phenol as claimed in claim 43 wherein the nitrating agent is nitric acid.

45. A nitrated phenol as claimed in claim 44 wherein there are zero optional substituents.

46. A nitrated phenol made by nitrating with a nitrating agent at least one compound of the formula

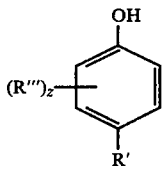

wherein R' is an aliphatic substituent having from about 40 to about 500 carbon atoms in a position para to the hydroxyl group; R''' is a member selected from the group consisting of lower alkyl, lower alkoxyl, nitro, halo, carboxy, carboxy ester of mono- and dihydric $C_{1-7}$ alkanols and carboxamide wherein the amide nitrogen can have up to 1 or 2 $C_{1-7}$ alkyl substituents; and z is 0 or 1.

47. A nitrated phenol as claimed in claim 46 wherein R' is derived from polymerized butylenes and mixtures thereof and z is zero.

48. A nitrated phenol as claimed in claim 46 wherein R' is an alkyl or alkenyl group derived from a homopolymerized or interpolymerized $C_{2-10}$ 1-mono-olefin and contains about 50 to about 300 carbon atoms.

49. A nitrated phenol made by nitrating with at least one nitrating agent and at least one phenol of the formula $(R)_a Ar'(OH)_c$ wherein R is an aliphatic substituent of at least about 40 carbon atoms; R is para to at least one —OH substituent attached directly to Ar'; c is 1 up to three times the number of aromatic nuclei in Ar', a is one and Ar' is a benzene moiety having 0 to 3 optional substituents selected from the group consisting of lower alkyl or halo or combinations of said optional substituents.

50. A nitrated phenol as claimed in claim 49 wherein R has an average of up to about 500 carbon atoms.

51. A nitrated phenol as claimed in claim 49 wherein the nitrating agent is selected from the group consisting of nitric acid, $NO_2$, $N_2O_3$, $N_2O_4$, $N_2O_5$, $NO_2Cl$, mixtures of alkali and alkaline earth metal nitrates with mineral acids, alkanoyl nitrates and mixtures thereof.

52. A nitrated phenol as claimed in claim 50 wherein R is hydrocarbyl and contains at least about 50 to about 300 carbon atoms.

53. A nitrated phenol as claimed in claim 52 wherein R is derived from homopolymerized or interpolymerized $C_{2-10}$ olefins and mixtures thereof.

54. A nitrated phenol as claimed in claim 53 wherein the nitrating agent is nitric acid.

55. A nitrated phenol as claimed in claim 54 wherein there are zero optional substituents.

56. A nitrated phenol made by nitrating with a nitrating agent at least one compound of the formula

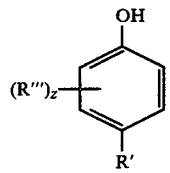

wherein R' is an aliphatic substituent having from about 40 to about 500 carbon atoms in a position para to the hydroxyl group; R''' is a member selected from the group consisting of lower alkyl; and z is 0 or 1.

57. A nitrated phenol as claimed in claim 56 wherein R' is derived from polymerized butylenes and mixtures thereof and z is zero.

58. A nitrated phenol as claimed in claim 56 wherein R' is an alkyl or alkenyl group derived from a homopolymerized or interpolymerized $C_{2-10}$ 1-mono-olefin and contains about 50 to about 300 carbon atoms.

59. A fuel or lubricant composition comprising a major proportion of a normally liquid fuel or a lubricating oil of lubricating viscosity and a minor proportion of the nitro phenol claimed in claim 1.

60. A fuel or lubricant composition containing a major proportion of a normally liquid fuel or a lubricating oil of lubricating viscosity and a minor proportion of the nitro phenol claimed in claim 12.

61. A fuel or lubricant composition containing a major proportion of a normally liquid fuel or a lubricating oil of lubricating viscosity and a minor proportion of the nitro phenol claimed in claim 19.

62. A fuel or lubricant composition containing a major proportion of a normally liquid fuel or a lubricating oil of lubricating viscosity and a minor proportion of the nitrated phenol claimed in claim 39.

63. A fuel or lubricant composition containing a major proportion of a normally liquid fuel or a lubricating oil of lubricating viscosity and a minor proportion of the nitrated phenol claimed in claim 46.

64. A fuel or lubricant composition containing a major proportion of a normally liquid fuel or a lubricating oil of lubricating viscosity and a minor proportion of the nitrated phenol claimed in claim 48.

65. A lubricant as claimed in claim 59.

66. A lubricant as claimed in claim 60.
67. A lubricant as claimed in claim 61.
68. A lubricant as claimed in claim 62.
69. A lubricant as claimed in claim 63.
70. A lubricant as claimed in claim 64.
71. A concentrate for treating lubricating oils or normally liquid fuels comprising a substantially inert solvent/diluent and at least one nitro phenol as claimed in claim 1.
72. A concentrate for treating lubricating oils or normally liquid fuels comprising a substantially inert solvent/diluent and at least one nitro phenol as claimed in claim 12.
73. A concentrate for treating lubricating oils or normally liquid fuels comprising a substantially inert solvent/diluent and at least one nitro phenol as claimed in claim 19.
74. A concentrate for treating lubricating oils or normally liquid fuels comprising a substantially inert solvent/diluent and at least one nitrated phenol as claimed in claim 39.
75. A concentrate for treating lubricating oils or normally liquid fuels comprising a substantially inert solvent/diluent and at least one nitrated phenol as claimed in claim 46.

* * * * *

UNITED STATES PATENT AND TRADEMARK OFFICE
CERTIFICATE OF CORRECTION

PATENT NO. : 4,347,148
DATED : August 31, 1982
INVENTOR(S) : KIRK E. DAVIS

It is certified that error appears in the above—identified patent and that said Letters Patent is hereby corrected as shown below:

In Column 22, Line 27: "claim 60" should read --claim 22--

In Column 23, Line 21: "$No_2$" should read --$NO_2$--

In Column 23, Line 26: "claim 32" should read --claim 42--

On TITLE PAGE, Line [54]: In the Title of Invention "FULL" should read "FUEL"

Signed and Sealed this

Nineteenth Day of October 1982

[SEAL]

Attest:

GERALD J. MOSSINGHOFF

Attesting Officer    Commissioner of Patents and Trademarks